United States Patent
Makarczyk et al.

(10) Patent No.: US 9,932,292 B2
(45) Date of Patent: Apr. 3, 2018

(54) PROCESS FOR WORKUP OF A CRUDE ESTER COMPRISING ESTERIFICATION CATALYST HYDROLYSIS PRODUCT IN SUSPENDED PARTICULATE FORM

(71) Applicant: BASF SE, Ludwigshafen (DE)

(72) Inventors: Piotr Makarczyk, Weisenheim am Sand (DE); Boris Breitscheidel, Waldsee (DE); Beatrice Rössler-Feigel, Weisenheim am Sand (DE); Kerstin Mühlheims, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/500,197

(22) PCT Filed: Jul. 29, 2015

(86) PCT No.: PCT/EP2015/067337
§ 371 (c)(1),
(2) Date: Jan. 30, 2017

(87) PCT Pub. No.: WO2016/016285
PCT Pub. Date: Feb. 4, 2016

(65) Prior Publication Data
US 2017/0267627 A1    Sep. 21, 2017

(30) Foreign Application Priority Data
Aug. 1, 2014 (EP) .................................... 14179461

(51) Int. Cl.
C07C 67/48  (2006.01)
C07C 67/56  (2006.01)

(52) U.S. Cl.
CPC .................................. C07C 67/56 (2013.01)

(58) Field of Classification Search
CPC .................................................... C07C 67/56
See application file for complete search history.

(56) References Cited

U.S. PATENT DOCUMENTS

| | | |
|---|---|---|
| 5,434,294 A | 7/1995 | Pugach et al. |
| 6,310,235 B1 | 10/2001 | Gick |
| 8,729,292 B2 | 5/2014 | Friese et al. |
| 2006/0270868 A1 | 11/2006 | Compton et al. |

FOREIGN PATENT DOCUMENTS

| | | |
|---|---|---|
| DE | 1945359 A1 | 3/1971 |
| DE | 2330435 A1 | 1/1975 |
| DE | 19721347 A1 | 11/1998 |
| EP | 1300388 A2 | 4/2003 |
| WO | WO-92013818 A1 | 8/1992 |
| WO | WO-9711048 A1 | 3/1997 |
| WO | WO-2010076193 A1 | 7/2010 |

OTHER PUBLICATIONS

International Search Report for PCT/EP2015/067337 dated Oct. 8, 2015.
Written Opinion of the International Searching Authority for PCT/EP2015/067337 dated Oct. 8, 2015.

*Primary Examiner* — Yevgeny Valenrod
*Assistant Examiner* — Blaine G Doletski
(74) *Attorney, Agent, or Firm* — Drinker Biddle & Reath LLP

(57) ABSTRACT

In a process for workup of a crude ester comprising esterification catalyst hydrolysis product in suspended particulate form, a) the crude ester is admixed in an emulsifying tank with 1% to 10% by weight of water and the water is emulsified in the crude ester to obtain a suspoemulsion, b) the suspoemulsion from the emulsifying tank is transferred to an agglomerating tank containing an initial charge of water-undersaturated crude ester, such that a water content below the solubility limit of water in the crude ester is established in the mixture of the suspoemulsion and the initial charge of crude ester, as a result of which the suspended particulate esterification catalyst hydrolysis products form stable agglomerates, and c) the agglomerates formed are filtered off.

14 Claims, 2 Drawing Sheets

Figure 1A:
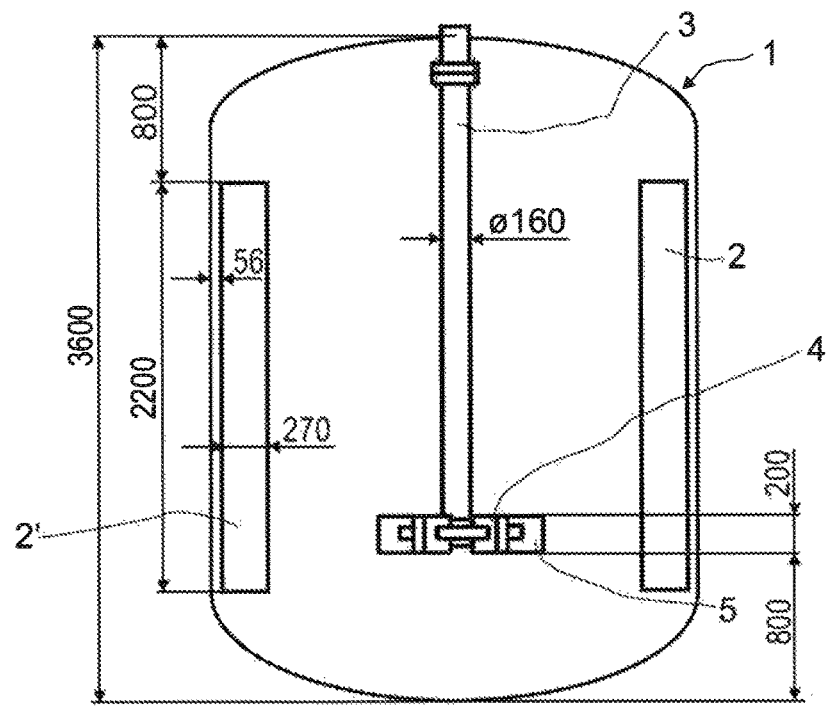

PROCESS FOR WORKUP OF A CRUDE ESTER COMPRISING ESTERIFICATION CATALYST HYDROLYSIS PRODUCT IN SUSPENDED PARTICULATE FORM

CROSS-REFERENCE TO RELATED APPLICATIONS

This application is a national stage application (under 35 U.S.C. § 371) of PCT/EP2015/067337, filed Jul. 29, 2015, which claims benefit of European Application No. 14179461.0, filed Aug. 1, 2014, both applications of which are incorporated herein by reference in their entirety.

BACKGROUND OF THE INVENTION

The invention relates to a process for workup of a crude ester of an esterification reaction catalyzed by a metallic esterification catalyst, wherein the crude ester comprises esterification catalyst hydrolysis products in suspended particulate form.

STATE OF THE ART

Esters of phthalic acid, adipic acid, sebacic acid or maleic acid find wide use in paint resins, as constituents of paints and especially as plasticizers for plastics.

It is known that carboxylic esters can be prepared by reacting carboxylic acids with alcohols. This reaction can be carried out autocatalytically or catalytically, for example by means of Brønsted or Lewis acids. In many cases, metal compounds are used as catalysts, such as the alkoxides, carboxylates and chelate compounds of titanium, zirconium, tin, zinc and aluminum.

Even though the catalytic properties of these metallic catalysts are satisfactory, the removal of the catalyst residues from the esterification products presents difficulties. For purification, the crude esters are generally first admixed with alkali metal hydroxides to neutralize unconverted or incompletely converted acid (partial esters), and the free alcohols are removed by steam distillation. After brief vacuum distillation to dry the product, the catalyst residues are then removed by filtration. Since the catalyst residues are generally of slimy, gel-like consistency, filtration is usually possible only with the aid of filtration aids, for example activated carbon, wood flour or kieselguhr. Nevertheless, such a filtration is still associated with serious disadvantages: long filtration times are required and the yield of ester is reduced because large amounts of product are retained in the filtercake.

WO 2010/076193 A1 discloses a process for workup of a crude ester from an esterification reaction catalyzed by a metallic esterification catalyst. The workup is effected by a) admixing the crude ester with an aqueous base at a temperature T of more than 100° C. under a pressure p which is equal to or greater than the vapor pressure of water at the temperature T, b) decompressing the ester-base mixture and evaporating off water, c) admixing the resulting liquid phase with water to form a water-in-oil emulsion, d) distilling water out of the emulsion and e) filtering the ester.

DE 194 53 59 discloses a process for workup of crude plasticizers, which has the following successive steps: (i) the residual acid in the crude plasticizer is neutralized with alkaline substances (e.g. 25% sodium hydroxide solution); (ii) the free alcohols in the crude plasticizer are removed by means of steam distillation; (iii) the product is cooled to temperatures below the boiling point of the water at the particular pressure; (iv) at least 0.5% by weight of water, based on the product to be worked up, is added; (v) the mixture of water and product to be worked up is stirred intensively at temperatures below the boiling point of the water at the particular pressure for at least 15 minutes; (vi) the water added is removed by vacuum distillation; (vii) the plasticizer is filtered. When the sodium hydroxide solution is added under the conditions specified, a significant portion of the water supplied with the aqueous alkali evaporates immediately, and so solid sodium hydroxide precipitates out. Solid sodium hydroxide reacts significantly more slowly than dissolved NaOH. In addition, the precipitation leads to deposits on pipelines and vessels, which necessitate frequent cleaning.

DE 23 30 435 describes a process for workup of crude esters, in which the crude ester at a temperature of 140 to 250° C. is neutralized under reduced pressure simultaneously with aqueous solutions of alkali metal or alkaline earth metal hydroxide, and subjected to a steam distillation by admixing with water under reduced pressure, then dried and the solid constituents formed are filtered off. The pressure and the rate of water addition should be regulated such that the water added evaporates rapidly.

Under the process conditions under which added water evaporates immediately, solid alkali metal or alkaline earth metal hydroxide can precipitate out, which leads to the above-described disadvantages. Since solid hydroxide reacts significantly more slowly, high base excesses are sometimes required for complete neutralization.

EP 1 300 388 discloses a process for preparing carboxylic esters, wherein the excess alcohol is removed after the esterification reaction, and the crude ester thus obtained is neutralized by addition of base and is then filtered. The alcohol is removed by at least one steam distillation and the base is added during a steam distillation. The alkali is to be sprayed into the reaction mixture at the bottom. As a result of the high temperature, the water evaporates. As a result of low rates of metered addition of the alkali, side reactions, for example the hydrolysis of the esters, are to be minimized. However, this has the disadvantage of long neutralization times and/or low throughputs.

U.S. Pat. No. 5,434,294 describes a process for titanate-catalyzed preparation of plasticizer esters. The product is treated with aqueous base and then filtered with the aid of a filtration aid, such as bleaching earth, hydrotalcite or magnesium silicate. The initial charging of a water-undersaturated crude ester, as a result of which the suspended particulate esterification catalyst hydrolysis products form stable agglomerates, is not known.

WO 97/11048 illustrates the preparation of mixed phthalic esters. The reaction of a phthalic monoester with a polyethylene glycol monomethyl ether is catalyzed with tetraisopropyltitanium. After the reaction has ended, sodium bicarbonate solution is added dropwise. After cooling, 2% water is added, volatile compounds, such as water and solvents, are distilled off under reduced pressure, and the mixture is filtered.

DE 197 21 347 discloses a process for preparing ester plasticizers, in which a mixture of acid or acid anhydride and alcohol is first allowed to react together at from 100 to 160° C. with removal of any water formed, the reaction is conducted to completion with addition of the catalyst and by increasing the temperature up to 250° C., the reaction mixture is reacted with an aqueous alkali metal or alkaline earth metal hydroxide solution, then the excess alcohol is removed, and the remaining crude ester is dried and filtered.

The alkaline treatment should appropriately immediately follow the esterification step without preceding cooling of the reaction mixture.

US 2006/0270868 A1 describes a process for purifying a crude ester from an esterification reaction which has been catalyzed with an esterification catalyst and a treatment with a basic aqueous alkali metal salt solution at a water content in the range from 0.7% to 1.4% by weight, based on the weight of the crude ester. Preference is given to using a titanium catalyst, which leads to an improvement in the filterability and in the purity of the ester prepared.

Known processes for workup of a crude ester comprising esterification catalyst hydrolysis product in suspended particulate form are still in need of improvement and often have the disadvantage of poor removability of the esterification catalyst residues, of long process times, of blockages and of failures of filter units and poorly regulatable process parameters.

It is an object of the present invention to specify a process for workup of a crude ester mixture which leads to esters having a low acid number with a high throughput and in good reproducibility, and in which the solid catalyst residues agglomerate within a short time and are obtained in a form having good filterability.

SUMMARY OF THE INVENTION

The object was surprisingly achieved by a process for workup of a crude ester comprising esterification catalyst hydrolysis products in suspended particulate form, in which
a) the crude ester is admixed in an emulsifying tank with 1% to 10% by weight of water and the water is emulsified in the crude ester to obtain a suspoemulsion,
b) the suspoemulsion from the emulsifying tank is transferred to an agglomerating tank containing an initial charge of water-undersaturated crude ester, such that a water content below the solubility limit of water in the crude ester is established in the mixture of the suspoemulsion and the initial charge of crude ester, as a result of which the suspended particulate esterification catalyst hydrolysis products form stable agglomerates, and
c) the agglomerates formed are filtered off.

The process according to the invention comprises a plurality of steps: an emulsification (step a)), an agglomeration (step b)) and a filtration (step c)).

The process can be conducted continuously, in which case the individual steps are performed in continuously operated apparatuses connected in series. Alternatively, the process can be performed batchwise.

DETAILED DESCRIPTION OF THE INVENTION

The process according to the invention proceeds from a crude ester comprising esterification catalyst hydrolysis products in suspended particulate form. This crude ester is generally obtained by admixing the esterification product of an esterification reaction catalyzed by a metallic esterification catalyst with an aqueous base and then evaporating water out of the esterification product/base mixture. By adding an aqueous base, the esterification catalyst used for synthesis is deactivated by hydrolysis and precipitated. At the same time, the acid and/or partial esters of the acid unconverted in the esterification reaction are converted to salts. The amount of aqueous base added is such that it is sufficient for complete neutralization of the acidic components of the crude ester. In practice, a greater or lesser excess of base is used. The total amount of the acidic components of the crude ester is appropriately covered by the acid number AN in mg KOH/g.

In a preferred embodiment, the crude ester, prior to the neutralization, has an acid number of less than 0.1 mg KOH/g crude ester. It has been found that continuous filtration of the agglomerates formed is possible only with very great difficulty, if at all, when the acid number is higher, since the filter medium becomes blocked. It is assumed that higher acid numbers result in the presence, after the neutralization, of relatively high concentrations of partial ester salts that act as emulsifiers. The partial ester salts probably accumulate in the aqueous phase and make it difficult for defined agglomerates to form. In addition, the partial ester salts remaining in the agglomerates after the removal of the visible water phase can alter the properties of the agglomerates, such that they are no longer filterable satisfactorily.

Preferably, 100% to 300% of neutralization equivalents are introduced with the aqueous base, based on the acid number of the crude ester, especially 130% to 220%. Neutralization equivalent is understood to mean the notional fraction of a base molecule that can bind a proton. In other words, an excess of base of up to 200% is used, preferably in the range from 30% to 120%.

Useful aqueous bases include solutions of hydroxides, carbonates, hydrogencarbonates of alkali metals and alkaline earth metals. Aqueous alkali metal hydroxide solutions are generally preferred. Aqueous sodium hydroxide solution is particularly preferred owing to its ready availability.

The concentration of the aqueous base is not critical per se, but the esters may be hydrolyzed at the introduction site of the base when concentrated alkali metal solutions are used. On the other hand, the concentration of the aqueous base should not be too low, since the water introduced with the aqueous base has to be removed again in the next step. Preference is therefore given to aqueous bases of moderate to low concentration, for example those having a concentration of 0.5% to 25% by weight, especially of 1% to 10% by weight. Aqueous sodium hydroxide solution having a concentration of 1% to 5% by weight is particularly preferred.

Preferably, the crude esterification product is admixed with the aqueous base at a temperature T of more than 100° C. under a pressure p equal to or greater than the vapor pressure of water at the temperature T. It has been found that sufficiently rapid and complete neutralization is achieved when the aqueous base is added at a temperature T of more than 100° C. under a pressure p equal to or greater than the vapor pressure of water at the temperature T. The crude esterification product present after the esterification reaction or after the removal of excess alcohol generally has an elevated temperature. It can optionally be cooled, but only if its temperature is still more than 100° C. The aqueous base is added under pressure conditions under which the water does not evaporate spontaneously. The base is therefore available for the neutralization reaction completely in dissolved liquid form. This accelerates the reaction and allows full conversion. If the aqueous base were to be added under lower pressure, water would evaporate and the dissolved base would precipitate out in solid form. The solid base would be available for the neutralization only with a significantly lower reaction rate, if at all.

In general, the crude esterification product has a temperature T of 120 to 185° C. The corresponding vapor pressure $p_{vap}$ of water can be taken from the table below or reference works known to those skilled in the art. The person skilled in the art is aware that the vapor pressure of solvents is influenced by dissolved substances or mixing phenomena. These influences can be neglected in the present context. For the purposes of the present invention, the emphasis is on the vapor pressure of pure water.

TABLE

Vapor pressure of water

| T [° C.] | $p_{vap}$ [bar] |
|---|---|
| 105 | 1.208 |
| 110 | 1.432 |
| 115 | 1.690 |
| 120 | 1.985 |
| 125 | 2.320 |
| 130 | 2.700 |
| 135 | 3.128 |
| 140 | 3.613 |
| 145 | 4.154 |
| 150 | 4.758 |
| 160 | 6.179 |
| 170 | 7.917 |
| 180 | 10.026 |
| 190 | 12.549 |
| 200 | 15.547 |

In general, the pressure p at which the aqueous base is added is higher than the vapor pressure $p_{vap}$ at the temperature T. The pressure p is preferably at least 1.1 times $p_{vap}$, especially at least 1.25 times $p_{vap}$. Pressures of more than 25 bar are costly and inconvenient to achieve in industry and are therefore not preferred.

The aqueous base can be added in any suitable manner. It is preferably added below the liquid surface of the crude esterification product. Suitable examples for this purpose are probes or nozzles provided on a vessel bottom or the vessel wall. The mixture is then mixed intensively, for example by means of stirrers or of a circulation pump.

In the case of continuous performance, the addition of base is appropriately performed by spraying the aqueous base into a stream of the crude esterification product. To homogeneously mix in the aqueous base, the mixed stream is conducted through at least one mixer. Useful mixers here are dynamic mixers or static mixers or combinations thereof. Static mixers are preferred. In terms of flow mechanics, the static mixers can be divided into turbulent and laminar mixers. In the case of the turbulent mixers, both free turbulence-generating mixing systems and those with internals are useful. The suitable static mixers include multiflux mixers, helical mixers, vortex mixers, gate mixers, Sulzer SMX mixers, Sulzer SMV mixers and Kenics mixers. In a suitable embodiment, the static mixer is a tube with a cross section-narrowing diaphragm. The pressure jump beyond the diaphragm generates turbulence, which leads to sufficient mixing.

After addition of the base, the water introduced with the aqueous base is removed. For this purpose, the crude esterification product admixed with the aqueous base is appropriately decompressed, for example to a pressure of less than 800 mbar, especially less than 250 mbar, for example in the range from 50 to 150 mbar. In this way, the water introduced with the aqueous base can be removed without excessively thermally stressing the crude ester. As a result of the decompression, the mixture separates into a liquid phase and a vapor phase. The vapor phase which is drawn off removes the water introduced with the aqueous base again. In addition to the water introduced with the aqueous base, this treatment usually also evaporates off a portion of the residual alcohol. The vapors comprising water and alcohol can be collected and condensed and discarded or sent to a reuse.

After the decompression, the liquid phase generally has a temperature of 130 to 200° C. For this purpose, it is possible to heat the liquid phase if required.

The type of decompression vessel is not critical. For example, the mixture can be decompressed into a stirred tank in which a further treatment of the liquid phase is effected.

To complete the evaporation of the water, preference is given to mechanically moving the liquid phase obtained in the decompression under reduced pressure over a residence time of, for example, from 5 minutes to 1 hour, especially from 10 to 40 minutes. Suitable stirrers for this purpose are of various designs, for example a crossbeam stirrer.

The esterification catalyst hydrolysis product present in suspended particulate form in the crude ester, as a precipitated solid, comprises essentially catalyst decomposition products and salts of unconverted acid or partial esters of polybasic acids, in a finely distributed form which is difficult to filter. The process according to the invention therefore envisages measures in which the fine particles are agglomerated to larger, readily removable particles.

To this end, in step a), the liquid phase is mixed with water in an emulsifying tank to form a suspoemulsion. The water is distributed as a disperse phase in the form of fine droplets in the liquid organic phase. It is assumed that the fine solid particles migrate to the interface between water droplets and surrounding organic phase and/or collect in the water droplets. The ternary mixture that forms is referred to as suspoemulsion in the context of the present invention; this is understood to mean an emulsion comprising a disperse aqueous suspension in a continuous oil phase.

In order that a separate water phase forms, the amount of water added must be greater than corresponds to the solubility of water in the organic phase. The water solubility in the organic phase depends on factors including the content of unconverted alcohol, since the alcohol acts as a solubilizer. The higher the alcohol content, the more water has to be added in step a). In the case of typical residual alcohol contents of 1% to 3% by weight, amounts of 1% to 10% by weight of water, preferably of 2% to 6% by weight of water, based on the weight of the crude ester, are generally suitable.

The emulsifying operation can be conducted with a suitable stirrer, stirrer/stator system or homogenizer in an emulsifying tank. The liquid water phase is divided here into fine water droplets. Suitable stirrers, which are also referred to as stirrer units, are selected from radial stirrers, especially crossbeam stirrers, gate stirrers, paddle stirrers, anchor stirrers, helical stirrers, MIG stirrers, disk stirrers, pitched blade stirrers, propeller stirrers, impeller stirrers, turbine stirrers, screw-shaped stirrers, half-moon stirrers and combinations thereof. Suitable stirrers having a high specific stirrer output are, for example, disk stirrers. Alternatively, particularly in the case of a continuous process regime, it is possible to use a mixing nozzle, in which water is added directly to the crude ester stream through a dispersing valve. In one embodiment, a vessel having a pumped circulation system with a circulation pump may also be provided for mixing.

It has been found that the volume-specific power input and/or the circumferential speed are critical for optimal emulsification. In a preferred embodiment, the water added is emulsified in step a) at a Reynolds number of more than $10^4$ with a volume-specific power input in the range from 0.25 to 2.2 kW/m$^3$, preferably 0.6 to 2.0 kW/m$^3$, in the crude ester. Lower power inputs than those specified lead to coarse unstable suspoemulsions that coagulate rapidly. Higher power inputs than those specified lead to highly disperse suspoemulsions which form very fine agglomerates in step b) that are filterable with difficulty, or in which no agglomerates are formed, since the droplet size of the suspoemulsion is smaller than or comparable to the primary particle size of the esterification catalyst hydrolysis products.

The power input of a mixer into a polyphasic system is a parameter known to those skilled in the art. In the context of the present invention, the power input for illustrative rotor/stator systems and for stirrers for is determined experimentally as described below.

For a rotor/stator stirrer system, an adiabatic stirred vessel is initially charged with an initial amount of a system to be stirred having one or more phase(s) and a density, and the rotor/stator stirrer system is placed in the stirred vessel. The starting temperature of the system to be stirred is measured, the rotor/stator stirrer system is started and the change in temperature with the introduction of shear forces into the system to be stirred by the rotor/stator stirrer system is measured over a stirring time t at a speed n of the rotor/stator stirrer system. In addition, the final temperature of the system to be stirred is measured. The data obtained are used to calculate the specific power input into the system to be stirred. The calculations which follow are carried out using the example of water as the system to be stirred.

The power input is calculated according to formula 1:

$$P=[(mW_{transverse}*cpW_{transverse}*\Delta T)+(\Delta mW*\Delta H_{transverse})]/t \qquad \text{Formula 1:}$$

where P is the power input in watts, $mW_{transverse}$ is the mean amount of water in kg, $cpW_{transverse}$ is the mean heat capacity of water in kJ/(kg*K), ΔT is the difference between the starting temperature and final temperature of the water in ° C., ΔmW is the difference between the starting amount and final amount of water in kg, $\Delta H_{transverse}$ is the mean enthalpy of vaporization of water in kJ/kg and t is the stirring time in s.

For systems having stirrer units (stirrer systems) the torque M in N*cm is measured in the reaction product for a given speed n in $min^{-1}$.

The power is calculated by the following formula 2 as follows:

$$P=M*2*pi*n \qquad \text{Formula 2:}$$

where M is the torque in N*m and n is the speed in $s^{-1}$.

Alternatively, the power of a stirrer can be determined via the power consumption of the stirrer drive, the power determined in this way including the drive energy losses and/or the frictional losses, especially as a result of friction in bearings and gaskets.

The power input P determined in formula 1 and/or formula 2 is used to calculate the dimensionless Newton power index Ne according to formula 3:

$$Ne=P/(\rho W*n^3*d_2^5) \qquad \text{Formula 3:}$$

where P is the volume-specific power input in watts, ρW is the density of water in kg/m$^3$, n is the stirrer speed in $s^{-1}$ and $d_2$ is the stirrer unit diameter in m.

In a turbulent flow region in stirrer systems, the Ne number is virtually constant. The dimensionless Reynolds number is determined by the following formula 4:

$$Re=n*d_2^2*(\rho/\eta) \qquad \text{Formula 4:}$$

where n is the stirrer speed in $s^{-1}$, $d_2$ is the stirrer unit diameter in m, ρ is the density of the system to be stirred in kg/n$^3$ and η is the dynamic viscosity of the system to be stirred in Pa*s.

For flow systems in which stirrers are used, a turbulent flow in the region of Reynolds numbers greater than 1000 can be assumed.

The following formula 5 applies the Newton number determined for water by the formula 3 to a specific system to be stirred having a specific density, taking account of the volume of the system to determine the volume-specific power input Ps:

$$Ps=Ne*(\rho s*n^3*d_2^5)/V \qquad \text{Formula 5:}$$

where Ps is the volume-specific power input in Watt/m$^3$, Ne is the dimensionless Newton power index, ρs is the specific density of the specific system to be stirred in kg/m$^3$ and $d_2$ is the stirrer unit diameter in m and V is the volume in m$^3$ of the liquid to be stirred.

The volume-specific power input Ps in watts is calculated with reference to the volume of the system to be stirred.

In a preferred embodiment, the water added is emulsified in the crude ester in step a) with at least one stirrer at a circumferential speed in the range from 2.8 to 6.2 m/s, preferably in the range from 3.3 to 5.6 m/s, more preferably in the range from 3.8 to 5.1 m/s.

In a preferred embodiment, the emulsifying tank has a cylindrical outline, concluded with a base and preferably with a lid. The base and lid shapes are selected from dished ends, hemielliptical ends, torispherical ends, flat ends, conical ends, ends for trays and lids according to the ASME Standard (American Society of Mechanical Engineering) and combinations thereof.

In a preferred embodiment, the emulsifying tank has a height/diameter ratio H/D within a range from 1 to 6, preferably in the range from 2 to 4. In the context of the present invention, the height/diameter ratio H/D of a vessel is understood to mean the ratio between the total vessel height H (including the base and the lid) and the vessel diameter D.

In a preferred embodiment, the emulsifying tank has baffles disposed on the inner vessel wall, especially in a number of 3 to 12, preferably of 4 to 8, per pressure and suction side.

In the context of the present invention, baffles are understood to mean flow-disrupting internals in stirred tanks. Baffles prevent the medium moved by a stirrer system from rotating as well within the stirred tank. Baffles are installed, for example, on the inner vessel wall or on the base within the stirred tank.

In a preferred embodiment, the emulsifying tank has baffles arranged on the inner wall of the vessel with a ratio of baffle width to vessel diameter in the range from 0.05 to 0.5, preferably in the range from 0.1 to 0.35. In the context of the present invention, baffle width is understood to mean the width of the baffle in the direction projecting from the inner wall of the vessel into the vessel.

In a preferred embodiment, the emulsifying tank has baffles disposed on the inner wall of the vessel with a baffle length in the range between half the emulsifying tank diameter and a maximum of the height of the emulsifying tank.

In a preferred embodiment, the emulsifying tank has a fill level, defined by the ratio of the liquid fill level $H_f$ relative to the total vessel height H, within a range from 0.5 to 0.9, preferably within a range from 0.6 to 0.8.

The water droplets of the suspoemulsion thus obtained generally have a mean particle size of more than 10 to less than 2000 μm, especially 200 to 1000 μm, determinable, for example, by laser diffraction methods.

Step a) is appropriately effected at approximately standard pressure.

For step b), water-undersaturated crude ester is initially charged in an agglomerating tank. "Water-undersaturated" means that the crude ester has a water content lower than the solubility of water in the crude ester under the conditions in the agglomerating tank. The water-undersaturated crude ester is capable of dissolving water without forming a discrete water phase. The initially charged water-undersaturated crude ester may, especially in a continuous or semi-continuous process regime, comprise agglomerates of esterification catalyst hydrolysis products.

The suspoemulsion from the emulsifying tank is then transferred, for example pumped over, into the agglomerating tank containing the initial charge of water-undersaturated crude ester. The relative amounts of initially charged crude ester and suspoemulsion, and the level of water undersaturation of the initially charged ester, are chosen so as to establish a water content below the solubility limit of water in the crude ester in the mixture of the suspoemulsion and initially charged crude ester. By virtue of the water level going below the solubility limit of water in the mixture, the water can no longer exist as a separate phase. Water is instantaneously removed from the water droplets, and the particulate esterification catalyst hydrolysis products suspended in the water droplets or arranged around the water droplets coalesce and form stable agglomerates, which are coarse particles of good removability.

The solubility of water in the crude ester depends on various factors, but especially on the content of unconverted alcohol and the temperature. Depending on the concentration, alcohol can act as a solubilizer. The solubility of water depends on the corresponding alcohol content. Through addition of (unesterified) alcohol, any desired solubility of water in the crude ester can therefore be established. Higher temperatures likewise promote the solubility of water. The temperature of the initially charged crude ester is therefore preferably 60 to 80° C., especially 65 to 75° C.

The suspoemulsion has to be transferred into the suspension comprising agglomerates in one stage and rapidly. In order to maintain the water unsaturation of the crude ester initially charged in the agglomerating tank in a continuous or semicontinuous process regime, the water dissolved has to be withdrawn continuously from the agglomerating tank, preferably by distilling off water continuously. Preference is given to avoiding nucleate boiling. To this end, the suspension can be conducted through an evaporator, for example a falling-film evaporator. Alternatively, the suspension can be moved mechanically, for example stirred, under reduced pressure. The stirring can be effected in the agglomerating tank, appropriately under relatively low-shear conditions. Excessive input of shear energy could divide the still-labile agglomerates of the solid catalyst residues again to unwanted fine particles. In a preferred embodiment, the suspoemulsion is mixed in the agglomerating tank with at least one mixer at a volume-specific power input of less than 0.2 kW/m$^3$.

Preference is given to distilling the water off at a temperature of from 60 to less than 100° C. and a pressure of less than 500 mbar. If desired, the dissolved water can also be distilled off in several steps in successive stirred vessels, in which case a lower pressure and/or a higher temperature than in the preceding step is employed in the second or further step. The transfer from a stirred vessel into the downstream stirred vessel is preferably effected under relatively low-shear conditions, for example by free overflow and not by pumped transfer. In the case of multistage performance of the removal of the dissolved water, it may be advisable to recycle crude ester from the last stage (i.e. crude ester having the lowest water content) into the agglomerating tank, in order to promote the water unsaturation of the initially charged crude ester in the agglomerating tank.

In addition to the water present in the suspoemulsion, a portion of the residual alcohol usually also distills off in the course of this treatment. The vapors comprising water and alcohol can be collected and condensed, and discarded or sent to a reuse.

After this treatment, the solid is present in readily filterable form; no fines get through the filtration in step c). The use of filtration aids is not required; their use is not preferred.

Crude ester with agglomerates suspended therein can be drawn off from the agglomerating tank and sent to a filtration unit. For filtration of the ester, all suitable filters are suitable, such as chamber filter presses, band filters, cartridge filters or pan filters. For a continuous process regime, particularly pan filters with centrifugal discarding of the filtercake are suitable. The solids removed are generally discarded.

Preferably, the suspension comprising agglomerates is filtered in the absence of free water. The agglomerates are hydrophilic; on contact with water, they break down again to non-filterable nanoparticulate solids. Free water can arise, for example, when the suspension comprises dissolved water. Through lowering of the temperature in the filtration step, for example in contact with cold filtration apparatuses, the water solubility in the crude ester is lowered and free water is formed. When semicontinuous filters are used, these have to be dried thoroughly after cleaning with water or steam, in order that no free water gets into the filtration process.

The solid can absorb water under a high relative air humidity, as a result of which the agglomerates break down and are converted to an aqueous paste which is filterable only with very great difficulty, if at all. In a preferred embodiment, step c) is therefore performed with exclusion of moisture, especially in an environment of dry gas and/or inert gas.

In a preferred embodiment, the filtrate from step c), as liquid phase of the suspension, is subjected to a stripping treatment selected from stripping with a vapor flow, especially a steam flow, or with an inert gas flow, especially with nitrogen, $CO_2$, helium, neon, argon and mixtures thereof.

The crude ester used in the process according to the invention originates from a customary esterification process. Such processes are known to those skilled in the art and are described in many patent publications. In these processes, at least one carboxylic acid and/or carboxylic anhydride is reacted with an alcohol or alcohol mixture. In many cases, the alcohol serves simultaneously as an azeotroping agent for the water of reaction which forms in the reaction and is therefore used in excess. Preference is given to removing the majority of the unconverted alcohol still present here from the crude ester before step a). The alcohol content of the crude ester used in step a) is generally less than 5% by weight, for example from 1% to 3% by weight.

In the esterification process, the acid components used are carboxylic acids and/or carboxylic anhydrides. In the case of polybasic carboxylic acids, it is also possible to use partly anhydrized compounds. It is likewise possible to use mixtures of carboxylic acids and anhydrides. The acids may be aliphatic, including carbocyclic, heterocyclic, saturated or unsaturated, and aromatic, including heteroaromatic.

The suitable carboxylic acids include aliphatic monocarboxylic acids having at least 5 carbon atoms, especially from 5 to 20 carbon atoms, such as n-pentanoic acid, 2-methylbutyric acid, 3-methylbutyric acid, 2-methylpentanoic acid, 2-ethylbutyric acid, n-heptanoic acid, isoheptanoic acids, 2-methylhexanoic acid, cyclohexanecarboxylic acid, n-octanoic acid, 2-ethylhexanoic acid, isooctanoic acids, n-nonanoic acid, 2-methyloctanoic acid, isononanoic acids, n-decanoic acid, isodecanoic acids, 2-methylundecanoic acid, isoundecanoic acid, tricyclodecanecarboxylic acid and isotridecanoic acid.

Additionally suitable are aliphatic $C_4$-$C_{10}$-dicarboxylic acids or anhydrides thereof, such as maleic acid, fumaric acid, maleic anhydride, succinic acid, succinic anhydride, adipic acid, suberic acid, trimethyladipic acid, azelaic acid, decanedioic acid, dodecanedioic acid, brassylic acid. Examples of carbocyclic compounds are: hexahydrophthalic anhydride (cyclohexane-1,2-dicarboxylic anhydride), hexahydrophthalic acid (cyclohexane-1,2-dicarboxylic acid), cyclohexane-1,4-dicarboxylic acid, cyclohex-4-ene-1,2-dicarboxylic acid, cyclohexene-1,2-dicarboxylic anhydride, 4-methylcyclohexane-1,2-dicarboxylic acid, 4-methylcyclohexane-1,2-dicarboxylic anhydride, 4-methylcyclohex-4-ene-1,2-dicarboxylic acid, 4-methylcyclohex-4-ene-1,2-dicarboxylic anhydride.

Examples of suitable aromatic dicarboxylic acids or anhydrides thereof are: phthalic acid, phthalic anhydride, isophthalic acid, terephthalic acid, or naphthalenedicarboxylic acids and anhydrides thereof.

Examples of suitable aromatic tricarboxylic acids or anhydrides thereof are trimellitic acid, trimellitic anhydride or trimesic acid; examples of a suitable aromatic tetracarboxylic acid or anhydride thereof are pyromellitic acid and pyromellitic anhydride.

Particular preference is given to using phthalic anhydride or adipic acid as the carboxylic acid component.

Preference is given to using branched or linear aliphatic alcohols having from 4 to 13 carbon atoms. The alcohols are monohydric and may be secondary or primary.

The alcohols used may originate from various sources. Suitable feedstocks are, for example, fatty alcohols, alcohols from the Alfol process, or alcohols or alcohol mixtures which have been obtained by hydrogenating saturated or unsaturated aldehydes, especially those whose synthesis includes a hydroformylation step.

Alcohols which are used in the esterification process are, for example, n-butanol, isobutanol, n-octan-1-ol, n-octan-2-ol, 2-ethylhexanol, nonanols, decyl alcohols or tridecanols prepared by hydroformylation or aldol condensation and subsequent hydrogenation. The alcohols can be used as a pure compound, as a mixture of isomeric compounds or as a mixture of compounds with different carbon numbers. For example, $C_9$/$C_{11}$ alcohol mixtures can be used.

Preferred starting alcohols are mixtures of isomeric octanols, nonanols or tridecanols, the latter being obtainable from the corresponding butene oligomers, especially oligomers of linear butenes, by hydroformylation and subsequent hydrogenation. The preparation of the butene oligomers can in principle be carried out by three methods. Acid-catalyzed oligomerization, in which, in industry, for example, zeolites or phosphoric acid on supports are used, affords the most branched oligomers. In the case of use of linear butenes, for example, a $C_8$ fraction is formed, which consists essentially of dimethylhexenes (WO 92/13818). A process which is likewise practiced worldwide is oligomerization with soluble Ni complexes, known as the DIMERSOL process (B. Cornils, W. A. Herrmann, Applied Homogenous Catalysis with Organometallic Compounds, page 261-263, Verlag Chemie 1996). In addition, oligomerization is practiced over fixed bed nickel catalysts, for example the OCTOL process (Hydrocarbon Process., Int. Ed. (1986) 65 (2. Sect. 1), page 31-33).

Very particularly preferred feedstocks for the inventive esterification are mixtures of isomeric nonanols or mixtures of isomeric tridecanols, which are prepared by oligomerizing linear butenes to $C_8$-olefins and $C_{12}$-olefins by the Octol process, with subsequent hydroformylation and hydrogenation.

Additionally suitable are alkylene glycol monoethers, especially ethylene glycol monoethers, e.g. ethylene glycol mono-$C_1$-$C_{18}$-alkyl ethers, such as ethylene glycol monomethyl ether, ethylene glycol monoethyl ether, ethylene glycol propyl ether, ethylene glycol monobutyl ether (2-butoxyethanol) and mixtures thereof; and polyalkylene glycol monoethers, especially polyethylene glycol monoethers, such as polyethylene glycol monomethyl ether.

Particularly preferred alcohols are 2-ethylhexanol, 2-propylheptanol, isononanol isomer mixtures, decanol isomer mixtures and $C_9$/$C_{11}$-alcohol mixtures, and also ethylene glycol monobutyl ether.

The esterification catalyst is suitably selected from alkoxides, carboxylates and chelate compounds of titanium, zirconium, tin, aluminum and zinc. Suitable esterification catalysts are tetraalkyl titanates, such as tetramethyl titanate, tetraethyl titanate, tetra-n-propyl titanate, tetraisopropyl titanate, tetra-n-butyl titanate, tetraisobutyl titanate, tetra-sec-butyl titanate, tetraoctyl titanate, tetra(2-ethylhexyl) titanate; dialkyl titanates ($(RO)_2TiO_2$, in which R is, for example, isopropyl, n-butyl, isobutyl), such as isopropyl n-butyl titanate; titanium acetylacetonate chelates, such as diisopropoxybis(acetyl-acetonate)titanate, diisopropoxybis(ethylacetylacetonate)titanate, di-n-butyl-bis(acetylacetonate)titanate, di-n-butylbis(ethylacetoacetate)titanate, triisopropoxidebis(acetylacetonate)titanate; zirconium tetraalkoxides such as zirconium tetraethoxide, zirconium tetrabutoxide, zirconium tetrabutyrate, zirconium tetrapropoxide, zirconium carboxylates such as zirconium diacetate; zirconium acetylacetonate chelates, such as zirconium tetra(acetylacetonate), tributoxyzirconium acetylacetonate, dibutoxyzirconium bis(acetylacetonate); aluminum trisalkoxides, such as aluminum triisopropoxide, aluminum trisbutoxide; aluminum acetylacetonate chelates, such as aluminum tris(acetylacetonate) and aluminum tris(ethylacetylacetonate). In particular, isopropyl n-butyl titanate, tetra(isopropyl) orthotitanate or tetra(butyl) orthotitanate are used.

The catalyst concentration is generally from 0.005% to 1.0% by weight based on the reaction mixture, especially from 0.01% to 0.3% by weight.

The alcohol to be converted, which serves as an azeotroping agent, can be used in a stoichiometric excess, preferably from 30% to 200%, more preferably from 50% to 100%, of the amount needed in stoichiometric terms.

The process according to the invention has the following advantages:

The process according to the invention assures stable agglomeration conditions which enable the process to proceed without disruption.

The process according to the invention enables the formation of agglomerates of good filterability, and prevents immediate blockage of filter fabrics.

The pressure drop over the filtercake rises more slowly, as a result of which filtration cycle lengths can be extended and the filters can be loaded to a higher level.

Initial charging of the water-undersaturated crude ester in the agglomerating tank achieves rapid and stable conversion of the water droplets comprising esterification catalyst hydrolysis products, neutralized monoester and excess base to the agglomerates, and prevents coagulation of the emulsion.

Setting a specific power input in the emulsifying tank achieves more effective conversion of the suspended particulate esterification catalyst hydrolysis products to the aqueous phase, and allows the water droplet size and hence the size of the agglomerates to be influenced and adjusted/controlled.

The esters thus prepared from polybasic carboxylic acids, for example phthalic acid, adipic acid, sebacic acid, maleic acid, and from alcohols, find wide use in paint resins, as constituents of paints and especially as plasticizers for plastics. Specific esters which can be worked up by the process according to the invention are plasticizers for PVC, such as dioctyl phthalates, diisononyl phthalates, diisodecyl phthalates and dipropylheptyl phthalates; plasticizers, for example for use in polyvinyl butyral, such as dibutyl glycol adipate, dioctyl azelate, dioctyl adipate, dibutyl sebacate, di(2-ethylhexyl) sebacate and dioctyl sebacate, and also dibutyl glycol phthalate.

FIGURES AND EXAMPLES

The invention is elucidated in detail by the appended drawings 1 and 2, and examples 1 to 4 which follow.

Figure 1B:
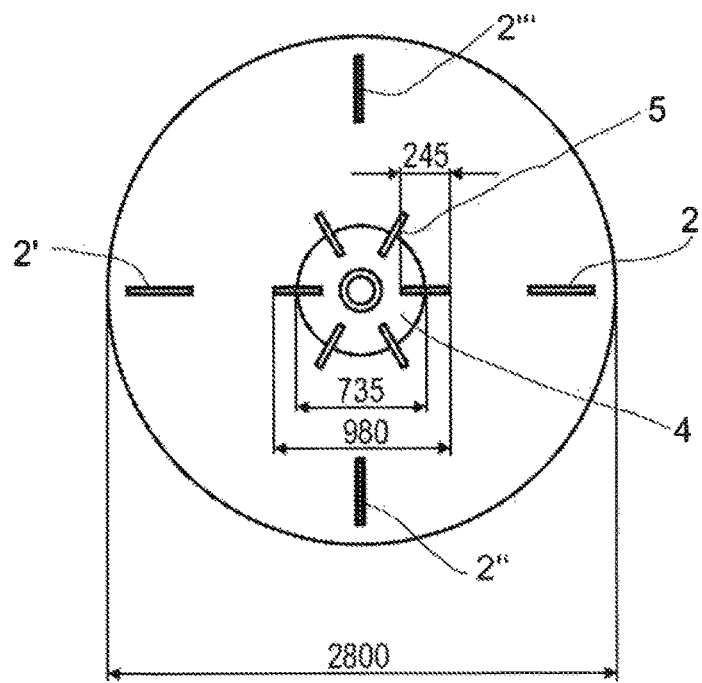
Figure 2:
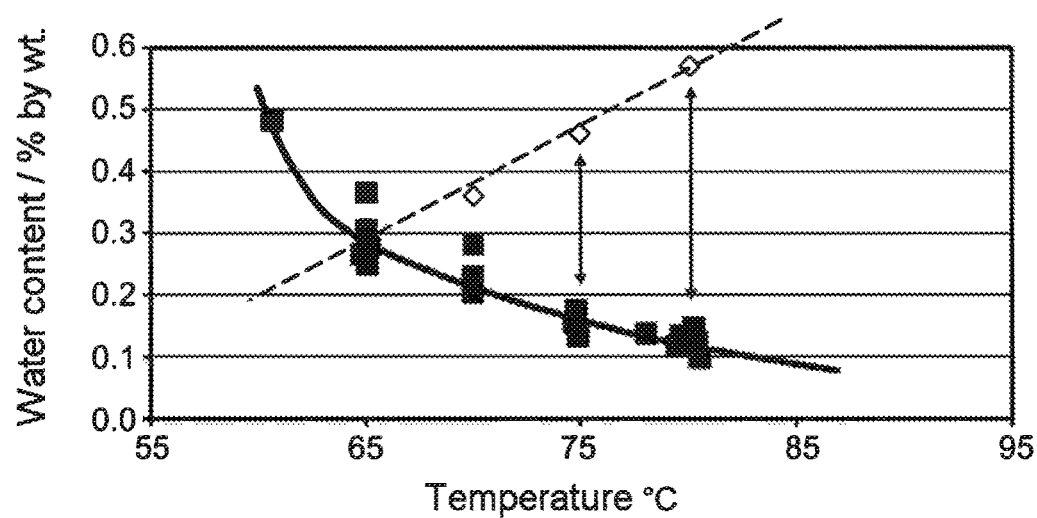

FIG. 1A: shows a schematic longitudinal section through an illustrative embodiment of an emulsifying tank for performance of step a) of the process according to the invention, FIG. 1B: shows a schematic cross section through an illustrative embodiment of an emulsifying tank for performance of step a) of the process according to the invention, FIG. 2: shows, by way of example, the relationship between temperature and water content of the crude ester and the solubility of water in the crude ester.

In FIGS. 1A and 1B, the following reference numerals are used:
1 emulsifying tank
2 first baffle
2' second baffle
2" third baffle
2'" fourth baffle
3 stirrer system
4 stirrer disk
5 stirrer blade FIG. 1 shows, by way of example, the construction of an emulsifying tank 1 for performance of the process according to the invention. The emulsifying tank consists of a vessel in which is disposed a stirrer system 3. By way of example, the stirrer system 3 is configured as a disk stirrer having a stirrer disk 4 with six stirrer blades 5 disposed thereon. Four baffles 2, 2', 2", 2'" are disposed on the vessel wall. As drive for the stirrer system 3, a 75 kW motor may be used, in order to achieve a specific power at the stirrer shaft in the range from 1 to 3.5 kW/m². The stirrer speed may especially be set within the range between 80 to 140 rpm. The measurements cited are examples of the height/diameter ratio H/D claimed in accordance with the invention and of the baffles disposed on the vessel wall.

FIG. 2 is described in detail in example 3 which follows.

Example 1

A stream of 20 000 kg/h of crude diisononyl isophthalate (DINP) having an acid number of about 0.05 mg KOH/g and an alcohol content of 2.0% by weight was worked up continuously.

The DINP stream having a temperature of about 150° C. was admixed under a pressure of 6 bar with 100 kg/h of 2% aqueous sodium hydroxide solution (corresponding to an about 200% excess, based on the acid number of the crude ester). The mixed stream passed through a mixing zone. Then the stream was decompressed into a stirred vessel to about 100 mbar. The residence time in the stirred vessel was about 0.5 h, during which the mixture was stirred with a three-level crossbeam stirrer at 160° C.

The mixture was pumped over into an emulsifying tank, as shown in FIG. 1, and cooled to about 80° C. in the process. The pressure in the emulsifying tank was ambient pressure. The stirrer used was a disk stirrer having 4 baffles with a specific power at the shaft in the range from 1 to 3.5 kW/m³ at the speed of 80 to 140 rpm. 800 kg/h of water (corresponding to 4% by weight, based on the crude ester stream) were added. The residence time in the emulsifying tank was about 0.5 h, during which the mixture was mixed vigorously with a disk stirrer (specific power input: 3 W/l) at 85 rpm.

The suspoemulsion was transferred at a temperature of 80° C. to an agglomerating tank in which an initial charge of dry diisononyl phthalate from prior production was present. In the agglomerating tank, the pressure was about 150 mbar. The residence time in the agglomerating tank was about 0.5 h, during which the mixture was stirred with a three-level crossbeam stirrer with a low power input of less than 0.1 W/l. The vapors comprising water and alcohol were drawn off. A steady-state water content of 0.12% by weight was established. This value is below the solubility limit at the given temperature and the given alcohol content.

The suspoemulsion was transferred to a further agglomerating tank at a temperature of 90° C. In the further stirred vessel, the pressure was about 100 mbar. The residence time in the further stirred vessel was about 0.5 h, during which the mixture was stirred with a three-level crossbeam stirrer with a low power input of less than 0.1 W/l. The vapors comprising water and alcohol were drawn off.

The product was fed continuously via an intermediate vessel to a filter and filtered through a Teflon fabric of pore size 10 μm.

This gave a clear product, entirely free of catalyst residues, having an acid number of 0.01 mg KOH/g, an alcohol content of 1.3% by weight and a water content of 0.1% by weight. By stripping with steam, it was possible to reduce the alcohol content to less than 0.01% by weight.

Example 2

Variation of the Stirrer Speed in the Emulsifying Tank

Example 1 was repeated with variation in the volume-specific power input and the circumferential speed of the stirrer in the emulsifying tank, by stepwise alteration of the rotational speed of the stirrer in the emulsifying tank between 55 to 120 rpm, as shown in table 1 below.

TABLE 1

Emulsifying tank parameters and agglomeration characteristics

| Revolutions [rpm] | Circumferential speed [m/s] | Volume-specific power input [kW/m³] | Observation* |
|---|---|---|---|
| 114 | 5.8 | 2.18 | (+) |
| 120 | 6.2 | 2.54 | (−) sample cloudy |
| 114 | 5.8 | 2.18 | (+) sample slightly cloudy |
| 110 | 5.6 | 1.96 | (+) |

TABLE 1-continued

Emulsifying tank parameters and agglomeration characteristics

| Revolutions [rpm] | Circumferential speed [m/s] | Volume-specific power input [kW/m³] | Observation* |
|---|---|---|---|
| 100 | 5.1 | 1.47 | (+) |
| 85 | 4.4 | 0.90 | (+) |
| 75 | 3.8 | 0.62 | (+) |
| 65 | 3.3 | 0.40 | (+) sample cloudy |
| 55 | 2.8 | 0.24 | (+) sample cloudy |

*(+): agglomerate formation
(−): no agglomerate was formed

The effect of increasing the rotational speed to 120 rpm was that no agglomerates were formed any more. The product obtained has a higher filter resistance compared to example 1. As a result, the filter is blocked within a short time and the workup has to be stopped. The lowering of the rotational speed to below 70 rpm led to a cloudy ester; the cloudiness indicates the presence of non-agglomerated esterification catalyst hydrolysis product. Aside from that, agglomerates were visible and the product was filterable.

Example 3

Variation of the Temperature in the Agglomerating Tank

Example 1 was repeated with variation of the temperature in the agglomerating tank in 5 K stages in the range between 60 to 80° C. Because of the variation in temperature, there was also a change in the water content, since less water vapor is drawn off at lower temperature at a constant pressure of about 150 mbar. At each of the temperature stages, samples were taken from the tank and analyzed for water and alcohol content. For all the samples, the alcohol content was between about 1.6 and 2% by weight. The water content is shown in FIG. 2 as a continuous curve. FIG. 2 also shows the solubility curve of water in the crude ester (at an assumed alcohol content of 2% by weight, shown as a dotted trend line through the unfilled rhombus points). Above the solubility curve, water is present as a discrete phase. Up to a temperature of 65° C. and a water content of 0.27% by weight, it was possible to filter product continuously, and the agglomerates formed were visible. If, however, the sample comprising the agglomerates is cooled to room temperature, the free water precipitates out of the solution and the agglomerates are broken down within seconds, forming a white, aqueous precipitate at the base of the sample bottle.

Comparative Example

The lowering of the temperature in the agglomerating tank in the method of example 3 to below 65° C. at a water content exceeding 0.5% by weight resulted in a shutdown of the agglomeration process. The product has a higher filter resistance compared to example 1. As a result, the filter is blocked within a short time and the workup has to be stopped. As can be seen in FIG. 2, at a temperature below 65° C. and a water content of 0.5% by weight, the solubility of water in the crude ester is exceeded and water is present as a discrete phase. Under these conditions no stable agglomerates are formed.

Example 4

Example 1 was repeated with variation in the acid number AN of the crude diisononyl isophthalate (DINP) in the range between 0.045 to 0.1 mg KOH per g of solution in the agglomerating tank. The amount of sodium hydroxide solution was adjusted such that the crude ester was fully neutralized (200% excess). Up to an AN of 0.09, it was possible to filter product continuously. At AN of 0.1, the product has a higher filter resistance compared to example 1. As a result, the filter is blocked within a short time and the workup has to be stopped.

The invention claimed is:

1. A process for workup of a crude ester product that includes an esterification catalyst hydrolysis product in suspended particulate form, the process comprising
    a) admixing the crude ester product in a tank with 1% to 10% by weight of water, based on the crude ester, and emulsifying the aqueous crude ester product to obtain a suspoemulsion, wherein the emulsifying of the aqueous crude ester product in step a) is achieved with at least one mixer at a Reynolds number of greater than $10^4$ with a volume-specific power input in the range from 0.4 to 2.54 kW/m³,
    b) transferring the suspoemulsion from the tank to an agglomerating tank containing an initial charge of water-undersaturated crude ester, wherein the water content is below the solubility limit of water in the combined mixture of the suspoemulsion and the initial charge of the water-undersaturated crude ester, upon which the suspended particulate esterification catalyst hydrolysis product forms stable agglomerates, and
    c) separating the agglomerates from the combined crude ester suspoemulsion product.

2. The process according to claim 1, wherein the crude ester has an acid number of less than 0.1 mg KOH/g crude ester.

3. The process according to claim 1, wherein the emulsifying the aqueous crude ester product in step a) with at least one stirrer at a circumferential speed in the range from 2.8 to 6.2 m/s.

4. The process according to claim 1, wherein the suspoemulsion obtained in step a) comprises distributed water droplets having a mean particle size of more than 10 μm to less than 2000 μm.

5. The process according to claim 1, wherein the tank has a height/diameter ratio H/D within a range from 1 to 6.

6. The process according to claim 1, wherein the water content in the agglomerating tank is maintained below the solubility limit of water in step b) by continually distilling off water.

7. The process according to claim 1, wherein the suspoemulsion is mixed in in the agglomerating tank with at least one mixer at a volume-specific power input of less than 0.2 kW/m³.

8. The process according to claim 1, wherein the the combined crude ester suspoemulsion product from step c) is subjected to a stripping treatment.

9. The process according to claim 1, wherein the suspended particulate esterification catalyst hydrolysis product is an esterification product of an esterification reaction catalyzed by a metallic esterification catalyst with an aqueous base from which a portion of water was removed from the esterification product/base mixture.

10. The process according to claim 9, wherein the aqueous base is added to the esterification product at a temperature T of more than 100° C. under a pressure p equal to or greater than the vapor pressure of water at the temperature T.

11. The process according to claim 9, wherein the water is from the esterification product/base mixture by decompressing the esterification product/base mixture.

12. A process for workup of a crude ester product, the process comprising
   a) admixing the crude ester product in an emulsification tank with 1% to 10% by weight of water, based on the crude ester product, and emulsifying the aqueous crude ester product to obtain a suspoemulsion, the emulsification conducted with a volume-specific power input in a range from 0.6 to 2.0 kW/m$^3$,
      wherein the crude ester is an esterification product of an esterification reaction catalyzed by a metallic esterification catalyst with an aqueous base from which a portion of water was removed from the esterification product/base mixture,
   b) transferring the suspoemulsion from the emulsification tank to an agglomerating tank that contains an initial charge of water-undersaturated crude ester product to provide a mixture of the suspoemulsion and the initial charge of the water-undersaturated crude ester, wherein the water content in the mixture is maintained below the solubility limit of water of the crude ester product with a continuous removal of water from the agglomerating tank, and upon which the suspended particulate esterification catalyst hydrolysis product forms stable agglomerates, and
   c) separating the agglomerates from the mixture of crude ester suspoemulsion product.

13. The process according to claim 12, wherein the mixture in the agglomerating tank is stirred with a mixer at a volume-specific power input of less than 0.2 kW/m$^3$.

14. The process according to claim 12, wherein the crude ester product has an alcohol content of 1 to 6 wt %, based on the crude ester product, and suspoemulsion of step a) comprises distributed water droplets having a mean particle size of more than 200 μm to less than 2000 μm.

* * * * *